US007750052B2

(12) United States Patent  (10) Patent No.: US 7,750,052 B2
Sorokin  (45) Date of Patent: Jul. 6, 2010

(54) METHOD FOR PRODUCING A WATER-ALCOHOL SOLUTION AND PRODUCTS BASED THEREON

(75) Inventor: Valery Nikolaevich Sorokin, Moscow (RU)

(73) Assignee: OOO "Naucho-Proizvodstvennoe Obiedinenie" "Opytnaya Vodno-Analitcheskaya Laboratoria", Moscow (RU)

( * ) Notice: Subject to any disclaimer, the term of this patent is extended or adjusted under 35 U.S.C. 154(b) by 152 days.

(21) Appl. No.: 10/471,246

(22) PCT Filed: Dec. 23, 2002

(86) PCT No.: PCT/RU02/00547

§ 371 (c)(1),
(2), (4) Date: Feb. 3, 2004

(87) PCT Pub. No.: WO03/062368

PCT Pub. Date: Jul. 31, 2003

(65) Prior Publication Data

US 2004/0109900 A1 Jun. 10, 2004

(30) Foreign Application Priority Data

Jan. 15, 2002 (RU) .............. 2002100464
Jan. 15, 2002 (RU) .............. 2002100465
Mar. 28, 2002 (RU) .............. 2002107883

(51) Int. Cl.
A61K 31/045 (2006.01)
A61K 31/34 (2006.01)
A61K 33/42 (2006.01)
A61K 33/18 (2006.01)
A01N 31/00 (2006.01)
A01N 43/08 (2006.01)
A01N 59/26 (2006.01)
A01N 59/00 (2006.01)

(52) U.S. Cl. .............. 514/724; 424/605; 424/666; 514/474

(58) Field of Classification Search .......... 424/605, 424/666; 514/724, 474
See application file for complete search history.

(56) References Cited

U.S. PATENT DOCUMENTS

| 2,879,165 | A | * | 3/1959 | Hendel | .............. 426/475 |
| 3,843,809 | A | * | 10/1974 | Luck | .............. 426/592 |
| 3,930,042 | A | * | 12/1975 | Dunnet | .............. 426/475 |
| 4,083,779 | A | | 4/1978 | Combe et al. | |
| 4,877,772 | A | * | 10/1989 | Mudzhiri et al. | .............. 514/23 |
| 2004/0013768 | A1 | * | 1/2004 | Khatchatrian et al. | .......... 426/11 |

FOREIGN PATENT DOCUMENTS

| EP | 0126691 | 11/1984 |
| GB | 958825 | 5/1964 |
| RU | 2035905 | 5/1995 |
| RU | 2064488 | 7/1996 |
| RU | 2106316 | 3/1998 |
| RU | 2124353 | 1/1999 |
| RU | 2130056 | 5/1999 |
| RU | 2133266 | 7/1999 |
| RU | 2136737 | 9/1999 |
| RU | 2137824 | 9/1999 |
| RU | 2154093 | 8/2000 |
| RU | 2154094 | 8/2000 |
| RU | 2154096 | 8/2000 |
| RU | 2154097 | 8/2000 |
| RU | 2154098 | 8/2000 |
| RU | 2154099 | 8/2000 |
| RU | 2154100 | 8/2000 |
| RU | 2157832 | 10/2000 |
| RU | 2159278 | 11/2000 |
| RU | 2159802 | 11/2000 |
| RU | 2166537 | 5/2001 |
| RU | 2167926 | 5/2001 |
| RU | 2169185 | 6/2001 |
| RU | 2174388 | 10/2001 |
| RU | 2175010 | 10/2001 |
| SU | 612956 | 6/1978 |

OTHER PUBLICATIONS

Gary Regan The Bartender's Bible 1999 pp. 170-171.*
English translation of front page of RU 2,154,093, dated Aug. 10, 2000.

(Continued)

Primary Examiner—Ernst V Arnold
(74) Attorney, Agent, or Firm—Ladas and Parry LLP

(57) ABSTRACT

The present invention relates to the field of food industry, where it may be used for producing alcoholic products, to pharmacology for producing infusions tinctures and extracts or preparations containing aqueous-alcoholic solutions as pharmaceutically acceptable media and also to cosmetology for producing cosmetic products containing aqueous-alcoholic solutions as cosmetically acceptable media. In the proposed process for preparing an aqueous-alcoholic solution, separation of harmful admixtures takes place due to the preliminary protonation separately of water and alcohol prior to the formation of the aqueous-alcoholic solution, this leading to improvements in the physicochemical and organoleptic characteristics of the final product. The process not only provides the possibility of preparing alcoholic beverages of improved quality, but also to shorten the production cycle in the case of preparing some of them (by as much as two times and more) and, as a consequence, to cut down the product costs.

17 Claims, No Drawings

OTHER PUBLICATIONS

English translation of front page of RU 2,154,094, dated Aug. 10, 2000.
English translation of front page of RU 2,154,096, dated Aug. 10, 2000.
English translation of front page of RU 2,154,097, dated Aug. 10, 2000.
English translation of front page of RU 2,154,098, dated Aug. 10, 2000.
English translation of front page of RU 2,154,099, dated Aug. 10, 2000.
English translation of front page of RU 2,154,100, dated Aug. 10, 2000.
English translation of front page of RU 2,167,926, dated May 27, 2001.
English translation of front page of RU 2,064,488, dated Jul. 27, 1996.
Partial English translation of front page of SU 612,956, dated Jun. 30, 1978.
English translation of front page RU 2,136,737, dated Sep. 10, 1999.
English translation of front page of RU 2,159,278, dated Nov. 20, 2000.
Partial English translation of front page of RU 2,166,537, dated May 10, 2001.
English translation of front page of RU 2,133,266, dated Jul. 20, 1999.
English translation of front page of RU 2,137,824, dated Sep. 20, 1999.
English translation of front page and claims of RU 2,130,056, dated May 10, 1999.
English translation of front page of RU 2,175,010, dated Oct. 20, 2001.
English translation of front page and claims of RU 2,157,832, dated Oct. 20, 2000.
English translation of front page of RU 2,169,185, dated Jun. 20, 2001.
English translation of front page and claims of RU 2,124,353, dated Jan. 10, 1999.
English translation of front page and claims of RU 2,174,388, dated Oct. 10, 2001.
English translation of front page and claims of RU 2,159,802, dated Nov. 27, 2000.
English translation of front page and claims of RU 2,106,316, dated Mar. 10, 1998.
English translation of front pages and claims of RU 2,035,905, dated May 27, 1995.
English language abstract and description of GB 958825, dated May 27, 1964.
English language abstract of EP 0126691, dated Nov. 28, 1984.

Definition of Ethanol. Large Encyclopedic Dictionary, "Chemistry", Moscow: Bolshaya Rossijskaya Entsiklopediya Publishers, 1998, p. 715.
*Eksoertiza Napitkov* [Examination of Beverages]. Poznyakovsky, V. M., Editor, Novosibirsk University Pubishers, 1999. pp. 17-18, 26, 63-69.
"Mathematical Models of Density Versus Water-Ethyl Alcohol-Sugar Mixture Composition Relationship", *Pishchevaya promyshlennost* [Food Industry], Moscow (2001), No. 6: pp. 62-63.
Ivanets, V. N. and V. G Menkh. "New Designs of Spiral-Screw Conveyors", *Pishchevaya promyshlennost* [Food Industry], Moscow (2001), No. 6: pp. 66.
*Pishchevaya tekhnologiya* [Food Technology], Moscow (2000), No. 5: p. 70.
Vuzov, Izvestiya. "Construction of a Model of the Properties of a Multicomponent Mixture by Using the Results of Expert Appraisal of Alternatives", *Pishchevaya teknologiya* [Food Technology], Krasnodar (2001), No. 1: pp. 57-59.
"Economical Preparation of Water", *Pishchevaya promyshlennost* [Food Industry], Moscow (2001), No. 3: p. 66.
"Non-Starchy Grain Carbohydrates and their Importance for Alcohol Production", *Pishchevaya promyshlennost* [Food Industry], Moscow (2000), No. 1: pp. 62-63.
"Computer Control of the Alcohol Production Process is the Future of the Alcohol Production Industry", *Pishchevaya promyshlennost* [Food Industry], Moscow (2001), No. 4: pp. 72-73.
"Alcoholic Beverage Products" [Likerno-Vodochnye Izdeliya], *Russian Collection of Standards*, Moscow (1994), pp. 12-14.
Vuzov, Izvestiya. "Application of Ultrafiltration Process for Continuous Saccharification in the Production of Ethanol", *Pishchevaya tekhnologiya* [Food Technology], Moscow (2001), No. 2-3: p. 41.
Palov, M. "Preparation and Use of Medicaments from Medicinal Plants", *Enclyclopedia of Medicinal Plants*, Moscow, 1988, p. 33.
Garnet, M. V. and A. N. Krechetnikova. "Technology of Producing Vodkas", *Pivo i Napitki* [Beer and Beverages], (2000), No. 1: 30-32.
Garnet, M. V. and A. N. Krechetnikova. "Technology of Producing Vodkas", *Pivo i Napitki* [Beer and Beverages] (2000), No. 2: 50-51.
Remy, H. *Lehrbuch der anorganishen Chemie*(1960), pp. 100-102.
"Acidity of Some Alcohols and Resolvation of Proton in $ROH-H_2O-H^+$ Systems", *Zhurnal Fizicheskoj Khimii* [Journal of Physical Chemistry], (1998), 72(5): 841-845.
Buhvestov, Urmas et al. "Solute-solvent and solvent-solvent interactions in binary solvent mixtures. Part 7. Comparison of the enhancement of the water structure in alcohol-water mixtures measured by solvatochromic indicators", *J. Phys. Org Chem.* (1998), 11(3): 185.
*Retseptury Likerno-Vodochnykh Izdelii i Vodok* [Formulas of Distillery Products and Vodkas], Moscow (1981), pp. 9-11, 311.
*Rastvory* [Solutions], K.P. Mishchenko, Editor. Leningrad: Izd. AN SSSR, 1959. p. 1092.

* cited by examiner

METHOD FOR PRODUCING A WATER-ALCOHOL SOLUTION AND PRODUCTS BASED THEREON

FIELD OF THE ART

The present invention relates to the field of food industry, where it may be used for producing alcoholic products, to pharmacology for producing infusions tinctures and extracts or preparations containing aqueous-alcoholic solutions as pharmaceutically acceptable media and also to cosmetology for producing cosmetic products containing aqueous-alcoholic solutions as cosmetically acceptable media.

STATE OF THE ART

Aqueous-alcoholic solutions are products in great demand in various fields of the art. This especially concerns production of a broad range of alcoholic products, production of infusions and extracts employed in pharmacology, which contain biologically active ingredients, production of various cosmetic products. The demand for said solutions stimulates constant improvements in their properties used in some product or other. It is desirable that the technology of making the product whose component part is an aqueous-alcoholic solution should undergo insignificant changes, this also fully applying to the procedure of preparing the aqueous-alcoholic solution as such.

It is known that small quantities of ethyl alcohol produce positive effect on human organism. Particularly favorable effect on human organism is produced by natural wines—nature-conditioned ethanol-containing liquids whose composition comprises, besides ethyl alcohol and water, biologically active components: organic acids, mineral substances, nitrogenous, pectin, tanning agents, vitamins (Bolshoj Entsiklopedicheskij Slovar' (Large Encyclopedic Dictionary), "Khimiya", Moscow, Bolshaya Rossijskaya Entsiklopediya Publishers, 1998, p. 715 (in Russian)).

However, land areas suitable for cultivating wine grapes are limited, and consumers' market cannot be saturated with wine. This is the reason why beverages made from food ethyl alcohol, containing at least fragrance and flavor agents and/or biologically active substances of various origin, water and sugar.

The range of alcohol and sugar concentrations in alcohol-water-sugar systems, which is of practical importance for alcoholic products is from 1-2 vol. % to 75 vol. %, mainly to 50 vol. % for alcohol and from 0 to 50% for sugar. This range encompasses all the wide assortment of distillery products produced by Russian and foreign manufacturers. The Russian official collection of the formulae of these products alone counts more than 280 names.

Depending on the strength, weight concentration of the total extract and sugar, distillery products are divided into 15 groups: liqueurs (strong, dessert, emulsion), cremes, cordials, punches, infusions (sweet, semi-sweet, semi-sweet low alcohol, bitter, bitter low-alcohol), dessert beverages, aperitifs, balsams and cocktails (V. M. Poznyakovskij (Ed.), "Ekspertiza Napitkov" (Examination of Beverages), Novosibirsk: Novosibirsk University Publishers, 1999, p. 63 (1) (in Russian); "Pishchevaya Promyshlennost'", Moscow, 2001, No. 6, pp. 63, 63; "Pishchevaya Tekhnologiya", Moscow, 2000, No. 5, p. 70 (in Russian).

Numerous publications related to aqueous-alcoholic beverages treat their compositions which comprise a mixture of semi-finished products (tinctures, juices, and the like) with an aqueous-alcoholic solution. So far, compositions of multicomponent beverages have been formulated mainly by way of empirical selection of ingredients, whose apt ratio is estimated by experts. At present an approach has been empirically developed, which makes it possible to systematize the results of investigations and simulate the properties of products being developed: constructing a model of the properties of a multicomponent mixture, based on the results of expert evaluation of alternatives, may be successfully used for determining the best beverage formulation (Izvestiya Vuzov, "Pishchevaya Tekhnologiya", Krasnodar, 2001, No. 1, pp. 57-59 (in Russian)).

As regards the technology of making alcoholic beverages, it reduces, mainly, to blending semi-finished products with an aqueous-alcoholic liquid and comprises new techniques and parameters of preparing the semi-finished products entering into the formulation of alcoholic beverages. The author has not found any principal innovations which affect the problem as a whole, except for new developments related to the preparation and purification of water and rectified ethyl alcohol, whose quality is in many respects decisive for the organoleptic properties of the final product ("Pishchevaya Promyshlennost'", 2001, No. 3, p. 66, ibidem, 2000, No. 1, pp. pp. 62, 63, ibidem, 2001, No. 4, pp. 72-73).

There are known numerous patents, wherein formulations of alcoholic beverages are disclosed, in which aqueous-alcoholic solutions are used, for instance:

there are known low-alcohol beverages, containing fragrance and flavor substances (aromatizers with taste and aroma of various fruits and berries, for example, "Raspberry", "Melon", "Pineapple", "Strawberry"), colorants, preservatives, and also rectified ethyl alcohol and water (RU Nos. 2154093-2154100);

a composition of ingredients according to Patent RU 2167926 is a sweet liqueur composition comprising a sea-buckthorn fruit drink, sugar, lactose, citric acid, color and an aqueous-alcoholic liquid up to strength of 17-25 vol. %.

a liqueur based on cowberry leafs, cranberry leafs with twigs, mint leafs, blackberry leafs, which contains a cranberry fruit drink and an aqueous-alcoholic liquid (Patent RU 2064488);

a composition of ingredients for an aperitif based on black chockeberry and cherry, comprises bitter almond, bird cherry, chamomile flowers, coriander seeds; contains an aqueous-alcoholic liquid serving both as an independent ingredient and for preparing infusions of black chockeberry and of a blend of chamomile flowers, almond, coriander seeds and bird cherry (Inventor's Certificate SU 612956);

a composition of ingredients for a gin, based on common juniper, coriander, anise, orange oil, orris-root and lovage contains rectified ethyl alcohol and water (Patent RU 2136737);

a method of aromatized vodka production, whose ingredients include citric acid, aromatizing agent BLACK CURRANT, sugar, lactose, and an aqueous-alcoholic liquid, is described in Patent RU 2159278;

a vodka, whose production process is protected by Patent RU 2166537, in addition to an aqueous-alcoholic liquid, comprises tartaric acid and ascorbic acid in combination with a sweetener, whereby said vodka acquires, along with good organoleptic characteristics, antitoxic properties.

In all the above-cited analogs which illustrate beverages of different kind, an aqueous-alcoholic solution is used, prepared by blending high-purity rectified alcohol with corrected purified potable water.

In none of patent information sources information could be found concerning any principally new techniques directed to eliminating negative consequences of warming-up which takes place when water is blended with alcohol and causes formation of toxic products which impair the physicochemical characteristics and organoleptic properties of the entire range of aqueous-alcoholic products and complicate the technology of their purification, this adding to the cost of production of the target product.

The technology of production of distillery products is described in detail in the above-cited reference "Examination of Beverages", pp. 63-69, wherein the requirements of the Russian Collection of Standards "Likerno-Vodochnye Izdeliya" (Distillery Products), Moscow, 1994 are taken into account. According to this technology, aqueous-alcoholic beverages having a strength of 12-60% are produced by blending preliminarily prepared semi-finished components: infusions, juices, aromatic alcohols, alcoholic solutions of ethereal oils with extra-purity rectified ethyl alcohol and conditioned potable water, and ripening the blend.

Water conditioning comprises a number of purification operations, depending on the quality of starting water: filtering through sand or ceramic filters, coagulation, settling, filtering through sand filters, softening by passing through ion-exchange resins (e.g., through a sodium cation-exchanger) or by a reverse osmosis water treatment with the help of semi-permeable membranes (ibidem, p. 26).

Ripening of the semi-finished products for a bouquet to be formed, for a better clarification of the beverage and enhancing its stability is carried out for 24-72 hours; sometimes the blend is homogenized, treated with cold, fining agent. The finished blend is filtered.

High-purity aqueous-alcoholic solutions used for the above-indicated purposes are prepared by blending rectified ethyl alcohol and purified potable water. The technology of purifying and preparing water for bottling, described in the journal "Pishchevaya Promyshlennost'", 2001, No. 3, p. 66, actually takes into account most of the latest achievements and comprises, if necessary, 7 steps:
 a) disinfection of starting water by chlorination;
 b) removal of iron ions;
 c) dechlorination (improving the organoleptic properties and clarification of water);
 d) softening of water (for example, with the help of sodium cation exchanger);
 e) desalination by means of reverse osmosis;
 f) adjustment of pH value; and
 g) disinfection of water before pouring it into containers by ultraviolet sterilization.

The water thus prepared corresponds to the main threshold limit values (color, hydrogen ion exponent, turbidity, content of iron, sulfates, sodium and potassium, total hardness).

Traditional technology of obtaining food ethyl alcohol is also progressing. The main trends here are, e.g.:
 further development of the process of producing alcohol according to the technology of using separately the liquid and solid fractions into which the starting boiled-soft mass separates; this shortens the fermentation time, reduces the consumption of steam and water in the step of distillation, makes it possible to use rationally costly enzymatic preparations in the step of saccharification, etc. (Izvestiya Vuzov, "Pishchevaya Tekhnologiya", 2001, No. 2-3, p. 41);
 further development of the process of biotransformation of the employed feedstock for producing high-quality alcohol ("Pishchevaya Promyshlennost'", 2000, No. 1, pp. 62, 63);
 development of computerized control of the alcohol production process ("Pishchevaya Promyshlennost'", 2001, No. 4, pp. 72-73) which makes it possible, in particular, to automate the technological process with a 6-8% increase of the yield of the target product and a 10-15% reduction of the prime cost.

There are many patents related, mainly, to the production of vodka and touching upon the problem of producing aqueous-alcoholic solutions. For instance, Patent RU 2133266 contemplates producing an aqueous-alcoholic mixture from alcohol of "Extra" grade and potable water with hardness not exceeding 0.36 mg-equiv./liter. The employed water is clarified with alumina and softened with the help of sodium cation exchanger. The method contemplates filtering an aqueous-alcoholic solution through a 4-meter high layer of activated carbon BOW and through sand filters with the rate of 40 dal/hr on fresh carbon and 30 dal/hr on regenerated carbon. The process contemplates also introducing into the aqueous-alcoholic solution sugar dissolved in water (in the production of vodka).

In accordance with patent RU No. 2137824 an aqueous-alcoholic solution is obtained with the use of water which has undergone reverse osmosis treatment.

In patent RU No. 2130056 (in the production of special ("osobaya") vodka, with a view to lowering the cost price while preserving the organoleptic properties of the target product, it is proposed to use for preparing an aqueous-alcoholic solution highest-purification rectified alcohol and softened water which has passed trough a sand filter and a carbon column on a fresh filter with carbon activity of at least 15 units.

In patent RU No. 2159278 an aqueous-alcoholic solution is prepared by blending rectified ethyl alcohol with purified potable water, followed by purifying the aqueous-alcoholic solution by modified starch; further, in the course of producing vodka in a finishing vat, the aqueous-alcoholic solution is added with a mixture of sugar in the form of its aqueous solution or a syrup with lactose (1.8-2.2 kg) and citric acid (0.2-0.4 kg per 1000 dal of finished product), preliminarily dissolved in purified water and kept for 20-24 hours at a temperature of 15-25° C.

In patent RU No. 2166537 which discloses a vodka production process, into a filtered aqueous-alcoholic solution a mixture of a sweetener with tartaric and ascorbic acids is added, in the following amounts: tartaric acid, 0.1-0.3 kg; ascorbic acid, 0.09-0.15 kg; and sugar substitute, 0.1-0.15 kg per 1000 dal of finished product.

In patent RU No. 2175010 an aqueous-alcoholic solution (for vodka production) is prepared by blending rectified ethyl alcohol with potable water treated by reverse osmosis, filtering the aqueous-alcoholic solution through active carbon and subsequent introducing an aqueous-alcoholic infusion of flax seeds in the course of blending ethyl alcohol with the treated water, and introducing a mixture of fructose and ascorbic acid at the final step of vodka production (5.5-6.5 kg of fructose and 0.04-0.06 kg of ascorbic acid per 1000 dal of vodka).

The main processes for preparing aqueous-alcoholic solutions and products based thereon are physicochemical processes of adsorption, diffusion and dissolution.

The first two of said processes are widely used in the practice of preparing aqueous-alcoholic liquids and products therefrom, which cannot be said about the process of dissolution—mutual dissolution of alcohol and water, about the dissolution or non-dissolution (precipitation) of admixtures present in both the starting water and alcohol and forming in the process of their blending. This particularly applies to an alcohol containing numerous admixtures which impair its taste and odor, many of these admixtures being toxic. Among volatile admixtures more than 70 various compounds were found, including higher alcohols that have bitter taste and sharp fusel smell, fusel oil alcohols, including n-propyl alcohol, n-butyl alcohol, n-amyl alcohol, etc., up to nonyl alcohol, as well as iso-alcohols corresponding to the above-said alcohols, mainly, isoamyl and isobutyl ones; aldehydes (acetaldehyde, formaldehyde, butyraldehyde, propionaldehyde, isovaleraldehyde, crotonic aldehyde, furfural, and others); ketones; esters (mainly ethyl acetate); acids (acetic, propionic, butyric, and others). Such admixture alcohols as methyl alcohol and propyl alcohol in small amounts are not felt by taste, but, being toxic, having accumulated in the organism, they cause serious poisonings ((V. M. Poznyakovskij (Ed.), "Ekspertiza Napitkov" (Examination of Beverages), Novosibirsk: Novosibirsk University Publishers, 1999, pp. 17, 18).

The problem of improving the mutual dissolution of alcohol and water is touched upon in patents RU No. 2157832 and No. 2169185, wherein a process for producing vodkas is disclosed.

According to patent RU No. 2157832 an aqueous-alcoholic solution is prepared by blending rectified ethyl alcohol with softened potable water, followed by purification of the resulting aqueous-alcoholic solution by passing it through a carbon cleansing battery, and filtration. Blending of alcohol and water is performed under turbulence conditions with the components moving in counterflow in a "pipe in the pipe" type mixer or in a special mixer of alcohol and water flows in a volume ratio of 1:1.38-1.44. Purification of the aqueous-alcoholic solution with active carbon is carried out under fluidized bed conditions. Filtration is carried out in three steps: first in a hydrocyclone, then through coarse frame flannel filters, and finally through a fine filter (hydrocompressed layer of quartz sand). The creation of turbulence owing to the counterflow provides favorable hydrodynamic conditions for mixing and dissolution of the alcohol in the water.

Patent RU No. 2169185 does not teach anything new about mixing under turbulence conditions. It is noted only that blending is carried out in a mixer till complete dissolution of alcohol in water.

In the specifications to the above patents it is explained that as highly stable system is obtainable by using an intensive intermixing with a definite ratio of alcohol and water flows. More concrete information and characteristics of the obtained products are not present.

No information can be found about particulars of preparing aqueous-alcoholic solutions in patents related to the pharmaceutical and cosmetic industry either, though aqueous-alcoholic solutions are widely used as pharmaceutically or cosmetically acceptable media in these industries as well.

For example, patent RU No. 2124353 discloses a topical pharmaceutical composition for skin treatment and care, which comprises in a cosmetically acceptable medium, namely, in an aqueous-alcoholic solution, at least one product with an irritant side effect.

Patent RU No. 2174388 teaches "Aromatizing and Refreshing Composition" comprising monomenthyl succinate in a cosmetically acceptable liquid—an aqueous-alcoholic solution. Furthermore, it is proposed to use this composition for preparing alcoholic beverages as well.

Aqueous-alcoholic solutions are also used as self-contained medicinal preparations (numerous tinctures, extracts and their combinations) (M. Palov, "Encyclopedia of Medicinal Plants", Russian translation by "Mir", Moscow, 1988).

In the journal "Pivo i Napitki" (Beer and Beverages"), 2000, No. 1, pp. 30-32 and No. 2, pp. 50, 51, in publications dealing with the production of alcoholic beverages, the problem of heat evolution when an alcohol is mixed with water is touched upon. This heat evolution tells negatively on the quality of the final product (there takes place additional evolution of fusel oils in the volume of liquid): the aqueous-alcoholic solution is prepared by blending a rectified highest-purity alcohol or "Extra" grade or "De luxe" grade alcohol with potable water (deodorized and softened) in a small-volume annular apparatus, wherein, due to the high turbulence of flow, optimal conditions for the alcohol dissolution are created. Final dissolution of the alcohol takes place in the cylindrical portion of the apparatus, whereto the aqueous-alcoholic solution comes through a diaphragm in the annular portion. The prepared aqueous-alcoholic mixture is filtered on sand filters to remove fine-dispersed particles which are formed from salts entrained with the water when it is blended with the alcohol. Then the aqueous-alcoholic mixture is treated with an adsorbent (for instance, with active carbon) for improving the taste properties and aroma of the mixture. In said publication it is reported that the preparation of the aqueous-alcoholic solution is accompanied by two phenomena: evolution of heat and reduction of the volume. The fact of the evolution of heat and reduction of the volume is explained by the authors by the formation of hydrogen bonds in mixed associates, i.e., in aqueous-alcoholic solutions: the origination of a hydrogen bond between the hydrogen atom of one molecule and the oxygen atom of another molecule of water due to electrostatic attraction of the proton (the hydrogen atom transfers an electron to oxygen) to the electron shell of another molecule of water. Similar phenomena occur between the alcohol molecules, because ethanol has affinity for water and similarly to water belongs to the category of associated liquids. The magnitude of the thermal effect upon blending ethanol and water is conditioned by the formation of crystalline hydrates which were mentioned for the first time by D. I. Mendeleyev (K. P. Mishchenko (Ed.), "Rastvory" (Solutions). Collection of papers, Leningrad, Izd. AN SSSR, 1959, p. 1163 (in Russian)), mixing them with one another or with an excess of one of the components (water or alcohol): when the weight concentration of the alcohol is smaller than 17.5%, hydrates $C_2H_5OH.12H_2O$ and excess water are present in solutions; in 17.5-46.0% solutions hydrates $C_2H_5OH.12H_2O$ and $C_2H_5OH.3H_2O$ are present; in 46.0-88.5% solutions hydrates $C_2H_5OH.3H_2O$ and $3C_2H_5OH.H_2O$ are present; when the content of alcohol is greater than 88.5%, hydrates $3C_2H_5OH.H_2O$ and excess alcohol are present. Besides, in the cited publication calculations are given of the amounts of alcohol and water to be supplied to the mixing apparatus for obtaining a definite strength of solution, with taking into account compression of the aqueous-alcoholic solution (maximum compression being in a 53.0-56.0% solution, maximum heat evolution being when the volume concentration of alcohol being 36.25 vol. % or 30 wt. %); however, no techniques are indicated, which would make it possible to decrease the negative effect of harmful admixtures present in the starting products and formed in the process of warming-up of the water-alcohol mixture on the final properties of the target products.

In the same publication it is indicated that intensification of the process of mixing alcohol with water is attained also by using other variants of mixing apparatus: cylindrical jet and injection apparatus. Owing to a small volume of these apparatus and particulars of feeding the components, the main requirement to the preparation of an aqueous-alcoholic solution is fulfilled: high degree of alcohol dissolution in water.

ESSENCE OF THE INVENTION

It is an object of the present invention is to provide a new process for preparing aqueous-alcoholic solutions of better quality by enhancing the dynamicity of solutions and ruling out warming up of the mixture of ethyl alcohol and water when blending thereof.

Another object of the present invention is to simplify the preparation of aqueous-alcoholic solutions by excluding the step of purifying the solution after blending.

Said objects are accomplished by that in a process for preparing an aqueous-alcoholic solution by blending purified potable water with rectified ethyl alcohol, which comprises a filtering step, before blending water with alcohol, a separate protonation of water and alcohol is carried out, followed by filtering the water and alcohol.

An additional, third object of the invention is to prepare aqueous-alcoholic solutions of better quality by raising the effectiveness of separate protonation of water and alcohol before blending thereof, owing to additional protonation carried out by intermixing separate flows of protonated water and protonated alcohol in glass or porcelain vessels, using glass or porcelain stirrers, respectively.

Still another object of the invention is to speed-up the process for preparing aqueous-alcoholic beverages with better physicochemical characteristics and organoleptic properties and, as a consequence, to make the technological process of preparing aqueous-alcoholic beverages cheaper.

This object is accomplished by that in a process for preparing an aqueous-alcoholic beverage, which comprises preparing semi-finished products and blending semi-finished products with high-purity rectified ethyl alcohol and conditioned potable water, followed by ripening the blend, separately protonated and filtered alcohol and water are used.

In accordance with the first and second aspects of the invention, protonation of water is carried out by introducing into water proton donors stronger than water, particularly inorganic acids, preferably orthophosphoric acid or carbonic acid, in an amount of 0.05-0.2 wt. %.

Protonation of ethanol is carried out by introducing acids stronger than ethanol as the proton donors. As such donors either organic or inorganic acids can be used, preferably hydrochloric acid or citric acid or ascorbic acid or oxalic acid, in an amount of 0.1-0.5 wt. %.

Boundary amounts of the introduced additives are determined by that when the amounts are lower than indicated above, an excess of protons is formed in the system, which is not sufficient for preventing warming-up of the aqueous-alcoholic mixture, while introducing additives in amounts exceeding the claimed values may adversely affect the organoleptic characteristics of products.

Separate filtering of protonated alcohol and protonated water may be effected, for example, by using reverse osmosis and Na-cationization technology.

The essence of the processes occurring in an aqueous-alcoholic system upon introducing proton donors, in our opinion, reduces to the following:

when water and alcohol are present simultaneously in the system, there takes place proton transfer from the alcohol to the water with formation of a hydroxonium ion $H_3O^+$,

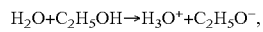

accompanied by the evolution of heat.

(The origination of hydroxonium in the aqueous-alcoholic solution brings about orientation of the liquid molecules around it and formation of a hydration-solvation shell, this causing loosening and degradation of the initial structure of the aqueous-alcoholic solution. The destroyed initial structure of water and alcohol, forming a hydration-solvation shell around hydroxonium, enters into chemical reaction with the molecules of alcohol or water, which reaction is accompanied by the evolution of heat, forming a complete set of aqueous complexes: $H_3O^+$, $H_5O_2^+$, $H_7O_3^+$, $H_9O_4^+$. These aqueous complexes were described for the first time by German chemist E. Wicke (this information can be found in H. Remy, Lehrbuch der anorganischen Chemie, Bd. 1, Leipzig, 1960).

when separately protonated water and alcohol are blended, the process of proton transfer from the alcohol to the water is inhibited due to the presence of excess protons in the system, and warming-up does not take place;

in the absence of excess protons in the alcohol-water system, there takes place complete mutual solubility of fusel oils and alcohol, while with protons in excess systems are formed, in which fusel oils are released from the alcohol and can be separated by filtration, for instance, with the use of reverse osmosis and Na-cationization.

At present investigations dealing with proton-containing aqueous-alcoholic systems are underway: it has been shown that the character of acid-base interactions in ROH—$H_2O$—$H^+$ systems, where R is H, $C_nH_{2n+1}$ or $C_2H_4OH$, determines the possibility of the proton being present simultaneously in different solvate forms $ROH_2^+$ and $H_3O^+$ and their relative concentration; a method has been proposed and augmented for calculating constants of proton resolvation in mixed solvents, particularly in aqueous-alcoholic systems, as a function of the temperature and nature of the solvent, and a dependence has been obtained of proton concentration in various solvate forms on the concentration of water, degree of electrolytic dissociation and temperature (Zhurnal Fizicheskoj Khimii, 1998, (72)5, pp. 841-845); complicated structures of water in aqueous-alcoholic mixed solutions, including the water-ethanol system, are being studied (J. Phys. Org. Chem., 1998, 11(3), pp. 185-192), etc. However the above-mentioned scientific studies have found no practical application in the technology of preparing aqueous-alcoholic solutions.

In accordance with the third aspect of the invention, the set object is accomplished by that in a process for preparing an aqueous-alcoholic solution based on purified potable water and rectified ethyl alcohol, which comprises separate protonation of water by introducing thereinto 0.05-0.2 wt. % of proton donors stronger than water and separate protonation of ethyl alcohol by introducing thereinto 0.1-0.5% of proton donors stronger than ethyl alcohol; separate filtering of the protonated water and ethyl alcohol, and blending thereof, the protonated water and water, before filtering are directed in separate flows into two cylindrical glass or porcelain vessels, wherein they are intermixed for 1-5 min with the help of glass or porcelain stirrers, respectively, rotated with the speed of preferably 1000-3000 rpm.

A stirrer of any type: paddle mixer, impeller mixer or anchor stirrer can be used, a paddle mixer with one or more paddles secured to the mixer axle being preferable.

The essence of additional protonation reduces to an additional number of protons being formed as a result of setting up turbulent motion of the liquid and the interaction of the solution components, particularly of water and alcohol, with silicon dioxide (which enters into the composition of the material of the vessel and stirrer), silicic acid $H_2SiO_3$ being thus formed, which under the conditions of a turbulent system is the source of protons:

$$H_2SiO_3 \to H^+ + HsiO_3^-.$$

Filtering of the separately protonated flows is carried out using the reverse osmosis technology.

In accordance with the first aspect of the invention, the set object is accomplished by that in a process for preparing an aqueous-alcoholic beverage, which comprises preparing semi-finished products and blending the semi-finished products with purified rectified ethyl alcohol and conditioned potable water, followed by ripening the blend, separately protonated and filtered alcohol and water are used.

For the protonation of alcohol, 0.1-0.5 wt. % of proton donors stronger than alcohols is introduced thereinto, for instance, organic or inorganic acids, such as hydrochloric acid, citric acid, ascorbic acid, oxalic acid; for the protonation of water, 0.05-0.2 wt. % of proton donors stronger than water is introduced thereinto, for instance, an inorganic acid, preferably orthophosphoric acid or carbonic acid.

A detailed technology of preparing semi-products of alcoholized juices, fruit juices, infusions and tinctures, aromatic alcohols, ethereal oils, corresponds to the technology disclosed in the above-cited reference "Examination of Beverages", pp. 63-69, Moscow, 1999.

In accordance with the present invention, the source of semi-products are various kinds of vegetable stock. For the provision of specific taste features, so called blending materials are used: sugar, honey, acids (including ascorbic acid and citric acid), colorants, etc. Alcoholized juices are prepared from comminuted stock by squeezing juice out of it and then preserving the juice with rectified alcohol to a strength of about 26% or with using alcoholized fruit juices, settling, and filtering. Alcoholized fruit juices are prepared by two- and more-fold steeping of fresh or dried fruit-and-berry stock with an aqueous-alcoholic solution. Alcoholized infusions are produced according to a similar technology by steeping lemon or orange peel, herbs, nuts, and the like. One kind of stock or a mixture of various components can be subjected to extraction, e.g., for preparing balsam infusions. The total duration of the processes is from 4-8 to 10-20 days. First- and second-decantation infusions and fruit juices are combined and filtered.

Aromatic alcohols comprising products of distillation with water-alcohol vapors of volatile aromatics from essential oil-bearing plant or fruit-and-berry stock, and also from semi-products based on this stock, are prepared by charging the stock into the distillation still of the apparatus and covering the stock with a 45-60% aqueous-alcoholic solution, and after short-time steeping distillation is carried out. Aromatic alcohols can be prepared from fruit juices and infusions.

Ethereal oils are extracted with solvents from plant stock, the solvent being then distilled-off.

Sugar syrup used for preparing a blend has the 65.8% concentration of dry substances for most distillery products and 73.2% for liqueurs.

The blend is prepared in collecting vessels, the ingredients being fed thereto in a definite sequence according to branch instructions. The blend is collected, then its physicochemical characteristics are checked and corrected, if required, by introducing lacking ingredients. For the beverage bouquet to be formed, its better clarification and stabilization, blends are ripened for 24-72 hours.

The invention will be further disclosed in detail in preferred embodiments thereof, which shall not be used for limiting the claims. Persons skilled in this field of the art will find possible numerous modifications which may be carried out within the scope of the inventive concept and which are also encompassed by the set of claims presented hereinbelow.

DETAILED DISCLOSURE OF THE INVENTION

It is known to introduce various acids playing the role of flavoring additives into aqueous-alcoholic solutions used for the preparation of alcoholic beverages. Such introducing does not take into account the physicochemical processes which occur in the volume of liquid aqueous-alcoholic solutions and tell on the quality of the final product. Introducing acids in the final step leads to the release of fusel oils and other admixtures into the volume of the final product, whereby its physicochemical and organoleptic properties are impaired.

For a detailed disclosure of the invention in accordance with its first and second aspects, five Examples were carried out, the information on which are summarized in Table 1. Examples 1-3 are carried out using citric acid as the most preferable proton donor for alcohol in amounts of from 0.1 to 0.5 wt. % and using carbon acid as the proton donor for water in an amount of 0.05-0.2 wt. %. Said amounts of both donors are also preferable ones. The alcohol to water ratio is selected such that the strength of the obtained aqueous-alcoholic solutions (alcohol concentration in volume percent) should be from 10 vol. % to 40 vol. %, this corresponding to beverages ranging from low-alcoholic ones to vodkas, though the process may be successfully used to both weaker and stronger beverages.

The processes according to all the presented Examples are carried out in the following manner: to alcohol and water placed into different (stainless steel) vessels corresponding donors are added with stirring in amounts required for their concentrations to be such as indicated in Table 1. In all the cases 1 kg of the aqueous-alcoholic mixture is taken without taking into account the amounts of proton donors. Then for Example 1 the amount of charged alcohol is 333.3 g, the amount of charged water is 666.7 g, and nitric acid and carbonic acid are charged in amounts of 0.333 g (0.1 wt. %) and 0.333 g (0.05 wt. %), respectively. Separate filtering of protonated alcohol and water is carried out by using sodium-cationization and reverse osmosis technologies. After that the filtered solutions are blended by adding water to the alcohol.

Examples 4 and 5, carried out similarly to Examples 1-3 but with the use of other proton donors, support the attaining of stable advantages offered by the proposed process in a broad range of alcohol concentrations: from 4 vol. % to 40 vol. %. The upper limit of 40 vol. % can be accounted for by the fact that the quality characteristics of 40% solutions can be compared with the GOST ratings established for vodkas (40% aqueous-alcoholic solutions).

When more concentrated solutions are used, the quality (purity) effect, compared with conventional aqueous-alcoholic solutions will be higher, because the main quantities of toxic products will be contained in the alcohol.

TABLE 1

| Components | Quantity, wt. % | | | | | | |
|---|---|---|---|---|---|---|---|
| | Examples in accordance with the invention | | | | | Control | Rating according to |
| | 1 | 2 | 3 | 4 | 5 | 6 | GOST 5964-93 |
| Rectified ethyl alcohol "Extra" (GOST 5962-67) Proton donors: | | | | | | | |
| citric acid | 0.1 | 0.3 | 0.5 | | | | |
| oxalic acid | | | | 0.3 | | | |
| hydrochloric acid | | | | | 0.3 | | |
| Corrected potable water (GOST P 51232-98) and Sanitary Regulations and Sanitary Code 2.1.4.1074-01 Proton donors: | | | | | | | |
| Carbonic acid | 0.05 | 0.1 | 0.2 | | 0.15 | | |
| Orthophosphoric acid | | | | 0.1 | | | |
| Alcohol:water volume ratio (%) | 40:60 | 20:80 | 10:90 | 4:96 | 40:60 | 40:60 | 40:60 |
| Alcohol:water weight ratio (%) | 33.33: 66.67 | 16.21: 83.79 | 7.99: 92.01 | 3.20: 96.80 | 33.33: 66.67 | 33.33: 66.67 | 33.33: 66.67 |
| Strength, vol. % | 40 | 20 | 10 | 4 | 40 | 40 | 40 |
| Weight concentration of aldehydes on conversion to acetaldehyde in 1 dm$^3$ of anhydrous alcohol, mg | 2.5 | 1.6 | 0.6 | 0.2 | 2.8 | 3.0 | 3 |
| Weight concentration of fusel oil on conversion to mixture of isoamyl and isobutyl alcohols (3:1) in 1 dm$^3$ of anhydrous alcohol, mg | 2.3 | 1.4 | 0.4 | 0.1 | 1.7 | 3.0 | Not over 3.0 |
| Weight concentration of esters on conversion to ethyl acetate in 1 dm$^3$ of anhydrous alcohol, mg | 21 | 16 | 11 | 0.6 | 18 | 25 | Not over 25 |
| Volume fraction of methyl alcohol on conversion to anhydrous alcohol, % | 0.027 | 0.021 | 0.020 | 0.018 | 0.027 | 0.03 | Not over 0.03 |
| Organoleptic evaluation | Colorless transparent liquids with characteristic aroma and taste | | | | | | |

Listed in Table 1 are also GOST ratings and the data of control Example 6 which was carried out without introducing proton donors into alcohol and water separately, but with carrying out adsorption with active carbon and double filtration—before and after blending water with alcohol (conventional process of preparing aqueous-alcoholic solutions).

All the prepared aqueous-alcoholic solutions were tested in accordance with GOST 5964-93 with regard to the main characteristics influencing the organoleptic properties of aqueous-alcoholic solutions. There were determined: weight concentrations of aldehydes (the determination was based on the reaction of aldehydes with fuchsin sulfurous acid); of fusel oil (the analysis was based on the reaction of higher alcohols with salicylic aldehyde solution in the presence of sulfuric acid); and of esters—products of the reaction of alcohols and acids (titrometric determination after their saponification with sodium hydroxide solution); and also the volume fraction of methyl alcohol (by comparing the color of typical solutions with the color of the solution being tested, which color originates in the reaction of methanol oxidation by potassium permanganate and sulfuric acid).

As is seen from Table 1, separate protonation and filtering of alcohol and water make it possible to improve the quality of prepared aqueous-alcoholic solutions, offering over the conventional technology:

1.1-1.5-fold lowering of the concentration of fusel oil;
1.15-30-fold lowering of the concentration of esters;
1.25-30-fold lowering of the proportion of aldehyde.

Data related to the third aspect of the invention (additional protonation) are summarized in Table 2.

TABLE 2

| Components, parameters of activation process, protonation process, and characteristics of prepared solutions | Quantity, wt. % | | | | | Rating according to GOST 5964-93 |
|---|---|---|---|---|---|---|
| | Examples | | | | | |
| | 7 | 8 | 9 | 10 | 11 | |
| Rectified ethyl alcohol "Extra" (GOST 5962-67) | 0.1 | 0.3 | 0.5 | 0.1 | 0.1 | |

TABLE 2-continued

| Components, parameters of activation process, protonation process, and characteristics of prepared solutions | Quantity, wt. % | | | | | Rating according to GOST 5964-93 |
|---|---|---|---|---|---|---|
| | Examples | | | | | |
| | 7 | 8 | 9 | 10 | 11 | |
| Proton donors: citric acid oxalic acid hydrochloric acid Corrected potable water (GOST P 51232-98) and Sanitary Regulations and Sanitary Code 2.1.4.1074-01 Proton donors: | | | | | | |
| Carbonic acid | 0.05 | 0.1 | | 0.05 | | |
| Orthophosphoric acid | | | 0.2 | | | |
| Weight alcohol:water ratio %) | 33.33: 66.67 | 16.21: 83.79 | 7.99: 92.01 | 33.33: 66.67 | 33.33: 66.67 | 33.33: 66.67 |
| Additional protonation: | | | | | | |
| stirring time, min | 3 | 1 | 5 | 3 | 3 | |
| mixer speed, rpm | 3000 | 2000 | 1000 | 3000 | 3000 | |
| material of vessel | glass | porcelain | glass | stn. steel | stn. steel | |
| material of stirrer | glass | porcelain | glass | stn. steel | glass | |
| Characteristics of prepared solutions | | | | | | |
| Strength, vol. % | 40 | 20 | 10 | 40 | 40 | 40 |
| Weight concentration of aldehydes on conversion to acetaldehyde in 1 $dm^3$ of anhydrous alcohol, mg | 1.5 | 1.0 | 0.4 | 2.4 | 2.0 | 3 |
| Weight concentration of fusel oil on conversion to mixture of isoamyl and isobutyl alcohols (3:1) in 1 $dm^3$ of anhydrous alcohol, mg | 1.8 | 0.9 | 0.3 | 2.2 | 2.0 | Not over 3.0 |
| Weight concentration of esters on conversion to ethyl acetate in 1 $dm^3$ of anhydrous alcohol, mg | 14.8 | 12.0 | 9.0 | 20.0 | 18.0 | Not over 25 |
| Volume fraction of methyl alcohol on conversion to anhydrous alcohol, % | 0.024 | 0.019 | 0.018 | 0.011 | 0.025 | Not over 0.03 |
| Organoleptic evaluation | Colorless transparent liquids with characteristic aroma and taste | | | | | |

Examples 7-9 illustrate the process in accordance with the invention, i.e., the preparation of aqueous-alcoholic solutions with the use of various (preferable) proton donors for alcohol and water, taken in the claimed (preferable) ratios, subjected to additional protonation carried out by intensive intermixing of protonated flows of alcohol and water, directed separately to cylindrical glass or porcelain vessels, using glass or porcelain stirrers respectively; the intermixing is performed during different periods of time and with different rotation speeds of the stirrers (preferable values of these parameters are presented). Examples 10-11 are control ones: in Example 10 additional protonation is carried out in a stainless steel vessel with a stirrer from the same material; in Example 11 a stainless steel vessel and a stirrer made from glass are used.

As is seen from Table 2, the proposed process makes it possible to additionally improve the quality of prepared aqueous-alcoholic solutions: a comparison of the characteristics of solutions prepared without additional protonation (Example 1) and with additional protonation (Example 7) shows that additional protonation provides:

22% lowering of the concentration of fusel oil;
30% lowering of the concentration of esters;
40% lowering of the proportion of aldehyde.

Additional protonation makes it possible to obtain more structured solutions, whereby mild gustatory sensations are provided. This effect is not noted, when separate protonation is performed in an apparatus manufactured from stainless steel.

In accordance with the fourth aspect thereof, the invention is illustrated by comparative Example 12, in which data are presented on the composition of the blend and on the characteristics of the product prepared in accordance with the recommendations given in the Collection of papers "Retseptury Likerno-Vodochnykh Izdelij i Vodok" (Formulas of Distillery Products and Vodkas), Moscow, 1981 (in Russian), pp. 9-11, 311 (control Example 12a) and analogous data obtained in accordance with the invention (Example 12b): the technology of preparing finished products is identical with the control, but contemplates the use of preliminarily protonated and filtered alcohol and water (sodium-cationization or reverse osmosis).

Example 12 a) A 25% strong lemon liqueur is prepared on the basis of an aromatic alcohol extracted from fresh lemon peel (180 kg) with the content of ethereal oil in the stock equal to 4.05 liter. Distillation with a 60% aqueous-alcoholic liquid (90 dal) gave 54 dal of 75% aromatic alcohol with the content of ethereal oil of 0.56 ml in 100 ml, the total content of the ethereal oil in the aromatic alcohol being 3 liters.

The composition of blend (in liters per 1000 dal):

| | |
|---|---|
| Aromatic alcohol from lemon peel, containing 3 liters of ethereal oil | 607.5 |
| 66% sugar syrup | 5156.0 |
| Highest-purity (96.2%) rectified ethyl alcohol | 2125.10 |
| Softened potable water | to make the volume equal to 1000 dal. |

The total time of preparing liqueurs is from 10 to 28 hours (p. 303).
Physicochemical characteristics of the liqueurs:

| | |
|---|---|
| Extract | 45 g/100 ml |
| Sugar | 45 g/100 ml |

Organoleptic characteristics: gold-colored liqueur with sweet taste and lemony aroma.

b) The content of the aromatic alcohol derived from lemon peel on conversion to 1 dal in the blend amounts to 0.61 liter.

Aromatic alcohol in the amount of 0.61 liter is obtained, starting from 0.122 kg of fresh lemon peel and 1.020 kg of a 60% aqueous-alcoholic solution of 96.2% ethyl alcohol: the aqueous-alcoholic solution contains 483 g of alcohol and 537 g of water. Before the preparation, the ethyl alcohol is protonated by adding 0.15 wt. % (0.72 g) of ascorbic acid and filtered (sodium-cationization and reverse osmosis); water is preliminarily protonated by adding 0.1 wt. % (0.54 g) of orthophosphoric acid and filtered (sodium-cationization and reverse osmosis).

For bringing the total volume of the blend to 1 dal (10 liters) 2.125 liters of 96.2% ethyl alcohol are required, this corresponding to 1.73 kg; the required amount of water is 2.065 liters (2.065 kg).

Preliminary protonation of ethyl alcohol before preparing the blend is carried out by introducing 0.15 wt. % (2.6 g) of ascorbic acid and filtering (sodium-cationization and reverse osmosis); water is preliminarily protonated by introducing 0.1 wt. % (2.065 g) of orthophosphoric acid and filtered (sodium-protonation and reverse osmosis).

For preparing 10 liters of a 25% lemon liqueur in accordance with the invention, a mixture is blended, containing:

| | |
|---|---|
| Lemon peel aromatic alcohol containing 3.4 ml of ethereal oil | 0.61 liter |
| 66.% sugar syrup | 5.2 liters |
| Ethyl alcohol containing 2.6 g of ascorbic acid | 2.125 liters |
| Softened potable water containing 2.065 g of orthophosphoric acid | 2.065 liters |

Total time of preparing the liqueur is 5-7 hours.
Physicochemical characteristics of the liqueur:

| | |
|---|---|
| Extract | 50 g/100 ml |
| Sugar | 45 g/100 ml |

The liqueur thus produced is characterized by a more saturated color, fine aroma of lemon, and tastes sweet. In its organoleptic characteristics it excels the known liqueur, because the influence of harmful admixtures on the taste and aroma of the liqueur is ruled out.

Examples 13-15 illustrate the use of aqueous-alcoholic solutions prepared in accordance with the proposed process in pharmaceutics and cosmetology, wherein aqueous-alcoholic solutions are widely employed for the preparation of infusions, tinctures, extracts and various medicaments for external use. Said products always contain active ingredients, which basically determine their characteristics. Aqueous-alcoholic solutions therein play mainly the role of pharmaceutically and cosmetically acceptable media. However, constituting a considerable (main) portion of the products, they also produce a essential effect on the quality of the products as a whole: the use of more pure aqueous-alcoholic solutions containing a smaller amount of toxic admixtures owing to protonation, in all cases of their use provides the obtaining of higher-quality products; in the case of infusions, tinctures and extracts protonation of the aqueous-alcoholic solution makes it possible, in addition to improving the quality, to shorten the time of steeping and extraction processes, reducing thereby the production price.

Example 13 a) Control. Preparing a valerian tincture producing sedative and regulatory effect on the cardiovascular system.

Comminuted and dried roots and rhizomes of valerian are wetted in a vessel provided with a ground stopper with a sufficient amount of a 60% aqueous-alcoholic solution (prepared on the basis of 96.2% ethyl alcohol). 5 hours later the swollen material is tightly stowed in a percolator with the drain valve open, adding such an amount of the aqueous-alcoholic solution that its layer above the surface of the material should be 35 mm. The liquid flown from the drain valve is poured back into the percolator, the drain valve is closed, and the percolator is allowed to stand for 24 hours. After that the percolation process is carried out slowly, so that during 1 minute 20 drops of the liquid should flow out. The percolate is collected and brought to the required volume with the same solvent. The total consumption of the aqueous-alcoholic solution was 1 kg.

b) By following the above-described procedure, a valerian tincture is prepared, using an aqueous-alcoholic solution prepared from separately protonated and filtered alcohol and water. The amount of alcohol in the solution is 473 g and the amount of rater is 527 g. The protonation of alcohol is effected by adding 0.15 wt. % (0.7 g) of ascorbic acid; the protonation of water is effected by adding 0.1 wt. % (0.53 g) of orthophosphoric acid.

For obtaining the product with an activity analogous to that of the tincture prepared as in Example 13a, but of a higher purity, it proved sufficient to carry out steeping for 12 hours, i.e., the required time proved to be half that used in the conventional procedure.

Example 14 a) Control. The preparation of a dentifrice water—a means for rinsing out the mouth after cleaning the teeth and food intake, which has not only hygienic, but also curative and prophylactic properties (strengthening of the gingivae and decreasing gingival hemorrhage.

A vessel with a 2 g batch of propolis is placed on a water bath for 15 minutes. Then slowly, during 10 minutes a 0.02 g batch of menthol is transferred thereto, thoroughly intermixing the contents with a glass rod. The mixture is cooled. Then added portion-wise to the vessel with the mixture of propolis and menthol, while stirring thoroughly, is an aqueous-alcoholic solution containing 31 g of ethyl alcohol of "Extra"

grade and 66.96 g of water, and the contents are thoroughly intermixed for another 40 minutes. The mixture is left to stand for 24 hours.

The dentifrice water thus prepared is a homogeneous transparent light-brown liquid with a pleasant odor. Clinical experimental investigations have revealed a disinfecting and anti-inflammatory effect of the dentifrice water. This dentifrice water does not produce allergizing or irritating effect.

b) By following a similar procedure, a dentifrice water is prepared from a protonated aqueous-alcoholic solution. The latter is prepared from 31 g of ethyl alcohol "Extra" preliminarily protonated with 0.1 wt. % (0.03 g) of citric acid and 66.98 g of purified water preliminarily protonated with 0.1 wt. % (0.067 g) of carbonic acid. The preliminarily protonated alcohol and water are additionally protonated by stirring separately alcohol and water in cylindrical glass vessels for 3 minutes with the help of glass stirrers rotating with the speed of 2000 rpm. After that filtering is performed by using sodium-cationization and reverse osmosis technologies.

The preparation of the dentifrice water analogous in its effectiveness to the dentifrice water according to Example 14a required twice less time (12 hours) for letting the mixture stand.

Example 15 a) Control. The preparation of a cosmetic composition (lotion) for face care, which cleanses the skin and stimulates blood circulation.

A lotion is prepared, containing 3 wt. % (3 g) of natural rose oil, 30 wt. % (30 g) of ethyl alcohol "Extra" and 67 wt. % (67 g) of purified water. First, an alcoholic solution of the aromatic ethereal oil is formed with the weight oil/alcohol ratio of 1:8; then to the resulting mixture an aqueous-alcoholic solution is added, comprising the rest of the alcohol and all the water. The obtained emulsion is filtered through a polymeric membrane. The obtained filtrate comprises a lotion which has an odor of rose oil, cleanses, softens and produces tonic effect on the skin.

b) A lotion is prepared by following the above procedure, but preliminarily alcohol and water are subjected separately to protonation. For the protonation of alcohol 0.3 wt. % (0.09 g) of oxalic acid is used, for the protonation of water 0.1 wt. % (0.067 g) of carbonic acid is used. The lotion thus prepared is characterized by improved softening properties owing to deeper penetration of the protonated liquid into skin integument.

ADVANTAGES OF THE CLAIMED INVENTION

It is known to introduce various acids which play the role of flavoring and flagrance additives into aqueous-alcoholic solutions used for preparing alcoholic beverages. The acid reacts with the formed aqueous-alcoholic product, wherein the processes of releasing fusel oils and other harmful admixtures into the volume of liquid have been completed. In the proposed process the separation of harmful admixtures takes place due to protonating separately water and alcohol prior to the formation of the aqueous-alcoholic solution, this leading to improvements in the physicochemical and organoleptic characteristics of the final product.

The proposed process not only provides the possibility of preparing alcoholic beverages and pharmaceutical and cosmetic products of improved quality, but also to shorten the production cycle in the case of preparing infusions and tinctures (by as much as two times and more) and, as a consequence, to cut down the product costs. Such considerable positive effect has become achievable owing to the principally new approach to the solving the general physicochemical problem of preparing aqueous-alcoholic solutions.

Aqueous-alcoholic solutions prepared in accordance with the proposed process may be widely used in alcoholic beverage industry in making low-alcohol products; they may find application in pharmacology in making preparations in the form of aqueous-alcoholic solutions, infusions, tinctures and extracts, and also in cosmetic industry as cosmetically acceptable media, since the requirements to aqueous-alcoholic solutions to be used for the indicated purposes are analogous. In all the cases of using protonated aqueous-alcoholic solutions their main effect—reduced toxicity—is provided.

The invention claimed is:

1. A process for preparing an aqueous-alcoholic solution, comprising the steps of:
    a) separate protonation of purified potable water and rectified ethyl alcohol to separately form protonated water and protonated ethyl alcohol, wherein said protonation of water is effected with the help of a first proton donor stronger than water and the protonation of ethyl alcohol is effected with the help of a second proton donor stronger than ethyl alcohol;
    b) separate filtration of the protonated water and the protonated ethyl alcohol from step (a) to form separate filtered products consisting of filtered, protonated water and filtered, protonated ethyl alcohol; and
    c) forming the aqueous-alcoholic solution from the filtered products from step (b) by blending the filtered, protonated ethyl alcohol and the filtered, protonated water; wherein the separate protonation in step (a) is effected with respective concentrations of the first and second proton donors effective to inhibit proton transfer from the rectified ethyl alcohol to the purified potable water after the blending and thereby to reduce an amount of impurities in the aqueous-alcoholic solution formed from the filtered, protonated ethyl alcohol and the filtered, protonated water as compared with an aqueous-alcoholic solution formed from ethyl alcohol and water that has not been subjected to the separate protonation and filtration in steps (a) and (b).

2. A process according to claim 1, wherein the second acid donor for ethyl alcohol is an organic or inorganic acid that is added to the ethyl alcohol in step (a) in an amount of 0.1-0.5 wt. %.

3. A process according to claim 2, wherein said second acid is selected from the group consisting of hydrochloric acid, citric acid, ascorbic acid or oxalic acid.

4. A process according to claim 1, which further comprises the step of a second protonation, carried out before step (b), wherein the protonated ethyl alcohol and protonated water are directed in separate flows to cylindrical glass or porcelain vessels, and separately agitating the separate flows with the help of stirrers made from glass and porcelain, respectively.

5. A process according to claim 4, wherein said separate agitating is carried out for approximately 1-5 minutes.

6. A process according to claim 4, wherein said separate agitating is carried out with the stirrers rotating with a speed of approximately 1000-3000 rpm.

7. The method according to claim 4, wherein the amount of impurities in the aqueous-alcoholic solution comprises a weight concentration of aldehydes on conversion to acetaldehyde in 1 $dm^3$ of anhydrous alcohol that does not exceed 2.4 mg, a weight concentration of fusel oil on conversion to a 3:1 mixture of isoamyl and isobutyl alcohols in 1 $dm^3$ of anhydrous alcohol that does not exceed 2.2 mg, a weight concentration of esters on conversion to ethyl acetate in 1 $dm^3$ of anhydrous alcohol that does not exceed 20 mg, and a volume fraction of methyl alcohol on conversion to anhydrous alcohol that does not exceed 0.025%.

8. A process according to claim 1, wherein the separate protonation of the purified potable water comprises adding a first acid to the purified potable water to form a first mixture, and the separate protonation of the rectified ethyl alcohol comprises adding a second acid to the rectified ethyl alcohol to form a second mixture.

9. A process according to claim 8, wherein the first acid is an inorganic acid that is added to the purified potable water in step (a) in an amount of 0.05-0.2 wt. %.

10. A process according to claim 9, wherein said first acid is orthophosphoric acid or carbonic acid.

11. A process according to claim 10, wherein second acid donor for ethyl alcohol is an organic or inorganic acid that is added to the ethyl alcohol in step (a) in an amount of 0.1-0.5 wt. %.

12. A process according to claim 11, wherein said second acid donor for ethyl alcohol is selected from the group consisting of hydrochloric acid, citric acid, ascorbic acid or oxalic acid.

13. A process according to claim 11, which further comprises the step of a second protonation, carried out before step (b), wherein the protonated ethyl alcohol and protonated water are directed in separate flows to cylindrical glass or porcelain vessels, in which the separate flows are agitated with the help of stirrers made from glass and porcelain, respectively.

14. A process according to claim 1, wherein the aqueous-alcoholic solution consists of the ethyl alcohol, water and impurities formed after the blending.

15. The method according to claim 1, wherein the amount of impurities in the aqueous-alcoholic solution comprises a weight concentration of aldehydes on conversion to acetaldehyde in 1 $dm^3$ of anhydrous alcohol that does not exceed 2.8 mg, a weight concentration of fusel oil on conversion to a 3:1 mixture of isoamyl and isobutyl alcohols in 1 $dm^3$ of anhydrous alcohol that does not exceed 2.3 mg, a weight concentration of esters on conversion to ethyl acetate in 1 $dm^3$ of anhydrous alcohol that does not exceed 21 mg, and a volume fraction of methyl alcohol on conversion to anhydrous alcohol that does not exceed 0.027%.

16. The process according to claim 1, wherein the process consists of steps (a), (b) and (c).

17. A process for preparing an alcoholic beverage comprising the steps of:
    (a) preparing the aqueous-alcoholic solution according to the process of claim 1; and
    (b) blending the aqueous-alcoholic solution with other components to form the alcoholic beverage.

* * * * *